United States Patent [19]
Kurbatov et al.

[11] Patent Number: 5,717,733
[45] Date of Patent: Feb. 10, 1998

[54] X-RAY AND NEUTRON DIFFRACTOMETRIC IMAGING OF THE INTERNAL STRUCTURE OF OBJECTS

[75] Inventors: Alexey V. Kurbatov, Moscow, Russian Federation; Pavel I. Lazarev, Menlo Park, Calif.

[73] Assignee: Quanta Vision, Inc., San Mateo County, Calif.

[21] Appl. No.: 454,909

[22] Filed: May 31, 1995

[51] Int. Cl.$^6$ ................................................. G01N 23/20
[52] U.S. Cl. ................................................. 378/71; 378/2
[58] Field of Search ................................................. 378/2, 71

[56] References Cited

U.S. PATENT DOCUMENTS

| | | | |
|---|---|---|---|
| 5,307,396 | 4/1994 | Tsuchino | 378/146 |
| 5,319,694 | 6/1994 | Ingal et al. | |
| 5,491,738 | 2/1996 | Blake et al. | 378/71 |

OTHER PUBLICATIONS

Mitrofanov, et al, "Method of Obtaining the Shadow of an object Internal Structure with the aid of Penetrating Radiation", *Naouka* Pub., 1982, pp. 221, 222.

Vinogradov et al., "Investigation of a Steering Mirror for the Soft X–Ray Region," Nuclear Instruments and Methods in Physics Research, 1987, pp. 11–12.

Vinogradov et al., "Turning a Ray of Soft X–Ray Radiation by Means of a Spherical Surface," (Russian publication, 13 Nov. 1985) pp. 594–596.

L. M. Soroko, "Gilbert's Optics," Nauker, 1981, pp. 34–37, 90–93, 126–127, 160–169, and 236–239.

*Primary Examiner*—Craig E. Church
*Attorney, Agent, or Firm*—Skjerven, Morrill, MacPherson Franklin & Friel; David T. Millers

[57] ABSTRACT

A method and device for examining the internal structure of an object uses diffracted X-rays or other penetrating radiation. In one embodiment, spatial filters proximate to a source of radiation transmit an array of divergent pixel-beams which irradiate an object being examined. The object absorbs, refracts, diffracts, and incoherently scatters radiation from the pixel-beams. Spatial filters proximate to a detector block undeflected and refracted radiation which exits the object. The detector separately measures diffracted radiation for each pixel-beam. For example, an integral of the diffracted intensity around a pixel-beam provides a pixel intensity in an image of the object. Alternatively, analyzing the intensity in a diffraction pattern around a pixel-beam can identify structures and materials within the object. A non-invasive procedure identifies abnormal tissue by measuring radiation diffracted at an angle characteristic of the diffraction pattern for abnormal tissue. In one embodiment of the invention, two spatial filters which form the pixel-beams have arrays of apertures with apertures in the first and second filters along lines from the source. This allow the pixel-beams to be divergent and increases the percentage of usable radiation from the source.

22 Claims, 4 Drawing Sheets

X-RAY AND NEUTRON DIFFRACTOMETRIC IMAGING OF THE INTERNAL STRUCTURE OF OBJECTS

BACKGROUND OF THE INVENTION

1. Field of the Invention

The present invention relates to using diffraction of penetrating radiation to image or analyze the internal structure of objects such as biological objects, plastics, metals, and other materials with ordered molecular or atomic structures.

2. Description of Related Art

When a beam of penetrating radiation such as X-rays or neutrons is incident on an object, the beam is affected by absorption and scattering. Conventional X-ray radiography forms images showing a pattern of absorption of X-rays in an object. In conventional radiography, scattering is a parasitic effect. Scattering has several distinct mechanisms such as non-coherent scattering, refraction, and diffraction. Recently, Mitrofanov (British patent publication 2317453), Belyaevskaya (PCT International publication WO 92/21016) and Wilkins (PCT International publication WO 95/05725) proposed approaches for refractive imaging of the objects.

The refractometric imaging systems of Mitrofanov and Belyaevskaya use detectors which rely on Bragg diffraction in crystals to detect refracted radiation. These systems require an initial beam with a high spectral purity (i.e. monochromatic radiation or radiation in a narrow spectral band) and a high spatial coherence (i.e. parallel radiation or radiation with a small angular divergence). Wilkins proposed a system which reduces the requirement for spectral purity by using an angle analyzer that does not rely on Bragg diffraction. Wilkins' system can use radiation with a wider wavelength band (a wider spectral range) because refraction does not strongly depend upon wavelength and the detector does not use Bragg diffraction which would introduce wavelength dependence.

The systems of Mitrofanov, Belyaevskaya, and Wilkins all detect radiation refracted in objects. Measuring the small angular deviations caused by refraction of penetrating radiation requires high spatial coherence of initial radiation and extremely accurate measuring devices. Narrow collimation of radiation from a source can provide a beam with high spatial coherence, but such narrow collimation uses only a small portion of the radiation from a typical source. Typically, only $10^{-3}$ to $10^{-4}$ of the total photon flux emitted by the source is usable. Accordingly, imaging a large object using a refractive system may require too much energy to be practical.

Imaging systems are needed that are more energy efficient and capable of quickly forming images of large objects.

SUMMARY OF THE INVENTION

Embodiments of the invention provide diffractometric imaging using radiation diffracted from objects containing chemical materials such as plastics, explosives, and crystals and biological materials such as muscle, mucus, cartilage, bones, hair, and feathers which have ordered atomic or molecular structures. One embodiment of the invention provides a method of imaging objects and performing an analysis of the structure and materials in objects. The method includes irradiating an object with a set of separate, divergent pixel-beams of penetrating radiation and detecting integrals of the intensity of diffracted radiation around each pixel-beam after the pixel-beam passes through the object.

Passing penetrating radiation through an array of apertures formed in a material that is non-transparent to the radiation forms pixel-beams. The separation between the apertures and therefore the initial separation between the pixel-beams should be large enough for a detector to resolve the distributions of intensity around each beam without interference from the diffracted intensity distributions of the neighboring pixel-beams. Allowing the pixel-beams to diverge from each other improves the detector's ability to resolve separate diffraction patterns and allows a greater portion of the flux from a radiation source to be used in imaging and analysis. For example, a hemishperical portion of the radiation flux can be divided into a set of pixel-beams that diverge by as much as 90° from the center of the radiation pattern.

For biological objects, typical apertures have diameter in a range from 20 to 100 microns and preferably within a range of from 20 to 60 microns. In order to increase sensitivity of the method, the radiation not deflected in the object and the refracted radiation which is deflected at small angles, in the range from 0 to 10 seconds of arc, are prevented from reaching the detector and hence are not detected. A filter, which includes an array of opaque regions placed in the path of the initial pixel-beams at a position between the object and the detector, can block the non-diffracted radiation. The size of the each opaque region corresponds to the size of a pixel-beam at the plane of the region plus a lateral extension to block radiation refracted from the pixel-beam.

An image of the object is formed from an array of pixels, each of which has an intensity determined from the intensity of diffracted radiation which is detected in the vicinity of a corresponding pixel-beam. The method also allows structural analysis of an object by detecting radiation distributions in diffraction patterns around the pixel-beams. The radiation distributions around a pixel-beam contains information about ordered materials along the path of the pixel-beam through the object.

The angular positions of reflexes and their corresponded intensity provides information about the structure of the material which produced the diffraction pattern. The diffraction pattern can be used for medical diagnostic purposes such as distinguishing normal tissues from abnormal tissues (such as cancer) in biological objects or in security applications for identifying particular chemical compounds (such as explosives or contraband) in luggage or other sealed containers.

As an alternative to forming pixel-beams, passing penetrating radiation though a spatial filter containing an array of opaque regions or barriers forms an incident radiation pattern having an array of shadowed regions. For example, if a first spatial filter contains an array of apertures which forms an array pixel beams. An alternative spatial filter, which is opaque (transparent) where the first spatial filter is transparent (opaque), forms a radiation pattern that is the "negative" of the pattern of radiation in the pixel-beams. Diffraction in an object deflects some radiation into the shadowed regions, and the pattern of diffracted radiation in each shadowed region can be analyzed in the same manner as the diffraction pattern around a pixel-beam described above.

One embodiment of the invention is an apparatus for imaging and/or structural analysis of objects. The apparatus includes: a source of penetrating radiation; an object holder; and a first spatial filter placed between the source and the object holder. The first spatial filter forms a spatially modulated pattern of penetrating radiation from the source. The spatially modulated pattern can contain divergent radiation from the source to increases to increase efficiency. Use of divergent radiation improves efficiency because the divergence angle determines the fraction of the total flux which is spatially modulated to form the incident radiation pattern. To improve collimation and spatial coherence of the spatially modulated pattern, a second spatial filter can be placed between first spatial filter and the object holder. The second spatial filter contains a pattern of opaque regions which is the same an a pattern in the first spatial filter but is expanded in size according to distance from the source. A third spatial filter between the object holder and a detector has opaque regions along the non-deflected path of radiation from the first spatial filter to block non-deflected radiation and provide a dark field imaging system.

BRIEF DESCRIPTION OF THE DRAWINGS

Use of the same reference symbols in different figures indicates similar or identical items.

DETAILED DESCRIPTION OF THE PREFERRED EMBODIMENTS

Figure 1:
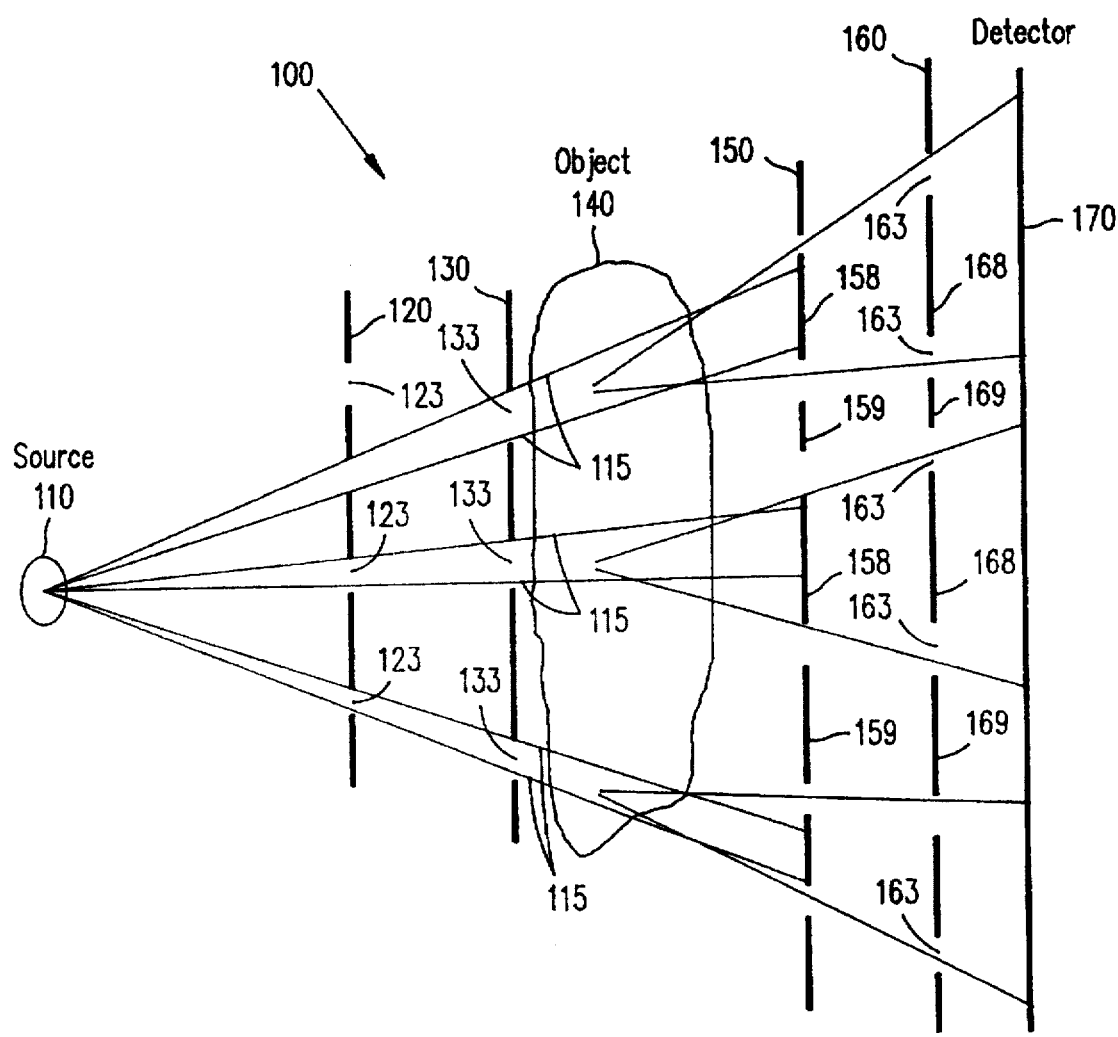
FIG. 1 is a diagram of an imaging apparatus in accordance with an embodiment of the invention.

Diffraction of radiation occurs when particles such as atoms, molecules, sub-molecular fragments in an object have structure with some degree of order on a scale about equal to the wavelength of the radiation. A perfect crystal is an example of a highly ordered structure. Gases have much less order. However even in a gas, molecules scatter radiation with a non-monotonic angular distribution about the direction an initial beam, and the distribution is characteristic of the molecules and supra-molecular clusters in the gas. Accordingly, the angular distribution of radiation scattered from a gas contains information about the structure of molecules in the gas and clusters which are formed by the molecules in the gas.

Diffracted radiation distributions are centro-symmetrical, and have characteristic patterns which can identify a material. Crystalline materials and many non-crystalline materials such as cellulose, mucus, muscle, cartilage, some plastics have ordered structure and distinct diffraction patterns. Other materials have diffusive diffraction patterns which still distinguish the degree of order in the structure. Distributions for some materials such as mucus and powdered monocrystals have circular maximums of intensity (or reflexes in the sense in which the term is used in the book "X-ray diffraction" by B. E. Warren, Dover Publication, Inc, N.Y.). Mucus has circular reflexes because the orientation of molecules in mucus is relatively random. Material like muscle which contains fibers oriented in one direction have meridional and equatorial reflexes. Highly ordered materials such as monocrystalline materials have spotlike reflexes in a symmetrical pattern.

The angular distribution, symmetry, and intensity of the diffraction pattern from a material indicates the structure of the material. If a material contains no prefer axis of orientation, a diffraction pattern is generally symmetric about a central axis of an initial beam and tends to contain separate circular reflexes. If the material has a distinguishable axis of orientation, the diffraction pattern tend to have axially variations and standalone reflexes of some form.

The angles of diffraction of X-rays from an ordered structure are governed by Bragg's equation, $\sin(\theta)=n*(\lambda)/(2*D)$, where $2\theta$ is the diffraction angle, n is an integer which is the order of diffraction maximum, $\lambda$ is the X-ray wavelength, and D is period of ordered structure, i.e. the distance between repeating fragments. The periodicity D of structures has different values for different materials, and the composition of the periodic structure and the angle $\theta$ determine the intensity of diffraction reflexes. For example, an intense reflex for mucus has periodicity D equal to 48 Å, and has angle $\theta$ equal to 0.9° at wavelength $\lambda$ of 0.71 Å. An intense reflex for one type of muscle is produced by periodic structure with periodicity D equal to 143 Å, which correspond to an angle e equal to 0.15°.

For X-rays, diffraction angles are typically orders of magnitude larger than refraction angles. Typical refraction angles for X-rays in most materials are less than about 10 arcsec, and typical diffraction angles are two to three orders of magnitude larger. In the above examples, the diffraction angles are about 540 arcsec for muscle and about 3000 arcsec for mucus. The large difference between scattering angles for diffraction and refraction means that equipment for measuring refracted radiation is often not suited for measuring diffracted radiation.

FIG. 1 shows an embodiment of an apparatus 100 for diffractive imaging and/or structural analysis of an object 140. Object 140 can be any type of object to be imaged or analyzed. A holder adapted for the type of object 140 under investigation places and fixes object 140 for exposure to multiple pixel-beams 115 from a radiation source 110. The term pixel-beam as used herein indicates a beam used to obtain information about structure of a portion of object 140 along the path of the beam. In one embodiment, each pixel-beam is used to obtain information for one pixel in an image or projection of object 140. In medical applications, object 140 could be a patient or a sample, and conventional devices for placing patients and samples can be used. In security applications, conventional holders such as for holding luggage during scanning for weapons or explosives would be used.

Radiation source 110 is a conventional source of X-rays, neutrons, or other penetrating radiation. Examples of sources of such radiation include a Roentgen tube, a synchrotron, or a radioactive source such as a cobalt 60 gun. In one embodiment, source 110 is an X-ray tube with a filter-monochromator which provides nearly monochromatic radiation, with a diameter of focus (bright spot) of about 6 to 10 microns. In one embodiment, source 110 is a microfocus source. Such X-ray sources are well known standard devices in radiology.

A first spatial filter 120 and a second spatial filter 130 are between source 110 and object 140. Spatial filters 120 and 130 are constructed of a material that is opaque to the penetrating radiation from source 110, and each of spatial filter 120 and 130 contains an array of apertures 123 or 133. Each of the apertures 123 has a corresponding aperture 133 which is centered along a line from source 110 through corresponding apertures 123 and 133. Apertures 123 and 133 have sizes on the same order of magnitude as the size of source 110, but each aperture 133 in spatial filter 130 is larger than the corresponding aperture 123 in spatial filter 120.

Figure 2:
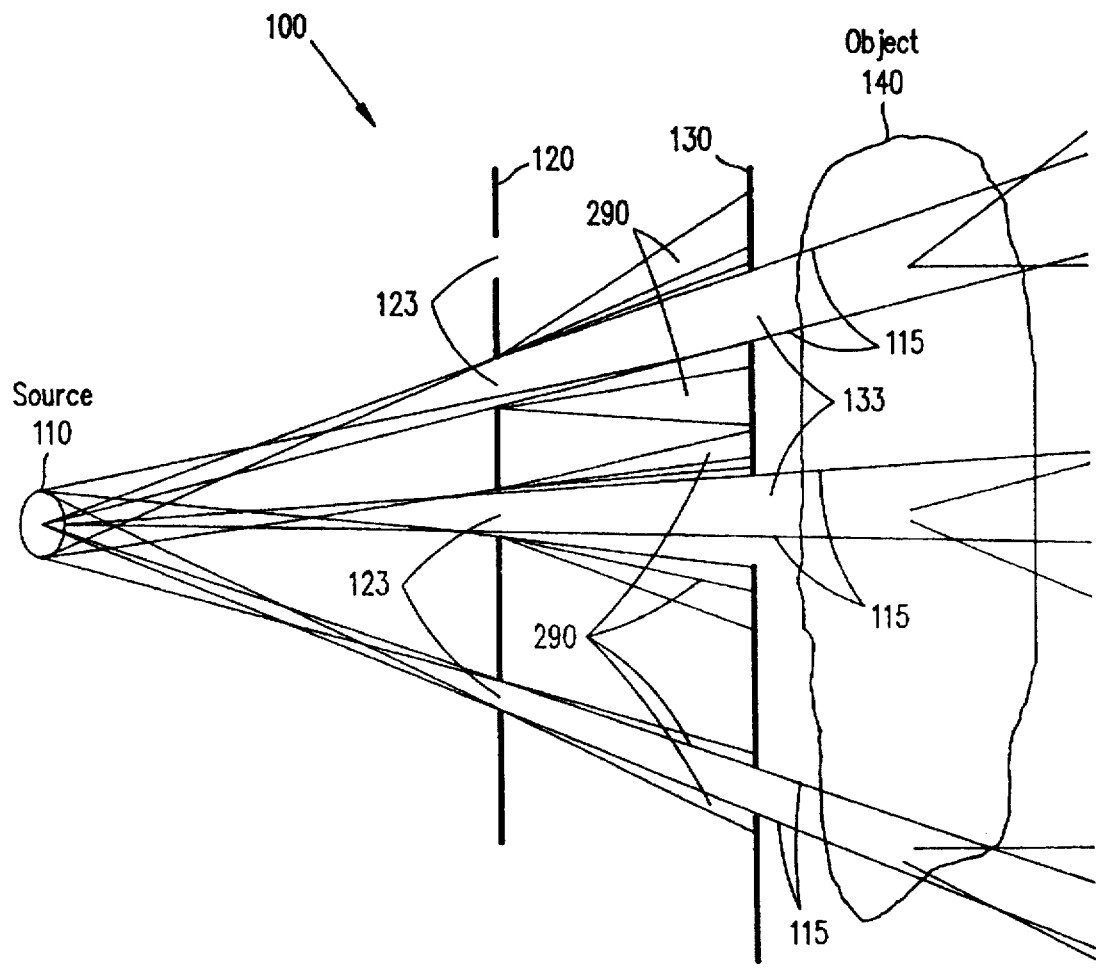
FIG. 2 illustrates the collimating part of the apparatus of FIG. 1.

Spatial filters 120 and 130 provide an array of pixel-beams 115 that are collimated in the sense that each pixel-beam has a minimal semi-shadow component 290 as shown in FIG. 2. Spatial filter 130 removes semi-shadow portion 290 of the radiation passing through filter 120 and radiation scattered or Fresnel diffracted by the edges of apertures in spatial filter 120. Spatial filter 130 is removed in some embodiments to increase the intensity of radiation in pixel beams 115 at the expense of increased angular spread and reduced spatial uniformity. Alternatively, one or more additional spatial filters containing progressively larger apertures can be placed between spatial filter 130 and object 140 to better remove radiation scattered at edges of apertures in preceding filters. Typically, the apertures in a spatial filter are circular with a diameter equal to the diameter of the pixel-beam at the plane of the filter, but any shape may be employed. For example, square apertures may increase the efficiency of the detector by increasing the amount of radiation from source 110 used for imaging.

In an exemplary embodiment where source 110 generates X-rays from the $K_\alpha$ line of molybdenum, at a wavelength of about 0.71 Å, spatial filter 120 contains a plurality of circular apertures with diameter about 10 to 2000 microns. In security applications such as luggage scanning, relatively large apertures (and pixel-beams) up to about 2 mm in diameter can be used. In medical applications where much higher resolution is desired, typical aperture diameters are from 10 to 50 microns. The aperture size is selected according to Fresnel diffraction effects and the desired resolution of apparatus 100. The material selected for spatial filters 120 and 130 should have high absorption at given wavelength. For example, copper or tin may be used to absorb X-rays with wavelength of 0.71 Å. Spatial filters 120 and 130 can be formed using conventional technologies for etching and/or laser drilling. Similar techniques with similar accuracy have been used in the manufacture of color CRTs for computer monitors.

Pixel-beams 115 diverge from each other. Divergence of pixel beams 115 from each other is useful because the spacing between the centers of the pixel beams increases with distance from source 110 and provides more space for detecting changes in the pixel beams caused by object 140. The additional space is useful in embodiments which analyze diffraction patterns for each pixel-beam. Additionally, central portions of pixel beams 115 pass unobstructed from source 110 to object 140, increasing the usable energy from source 110 when compared to systems which require pixel beams to be nearly parallel to each other. Source 110 can be placed closer to spatial filter 120 to provide greater divergence and a more compact measuring system. Using divergent beams utilizes a larger fraction of the output energy from source 110. For example, beams with a 45° divergence enable the use of up to about 8% of the total flux from source 110. In some systems which rely on refraction, the beams are nearly parallel and typically contain less that $10^{-4}$ of the radiation from a source.

A further efficiency provided by detecting diffracted radiation is that more divergence is permitted in each individual beam. Divergence in a beam tends to blur an image but is acceptable when the divergence is less than the angles being detected. Diffraction angles are relatively large when compared to the refraction angles used by some other system. Because diffraction angles are relatively large, some embodiments of the invention use divergent pixel-beams, and tolerate small distance between source 110 and spatial filter 120. The distance between source 110 and spatial filter 120 can be one the order of centimeters and provide each pixel beam with a divergence greater than typical angles of refraction.

The separations of centers of apertures 123 in spatial filter 120 are selected according to whether an image is formed and/or diffraction patterns are analyzed. For analysis of diffraction patterns, apertures 123 should be separated from each other by a distance which allows measurement of separate diffraction patterns for each pixel-beam 115. The optimal distance between centers of neighboring apertures 123 depends on the divergence of pixel-beams 115 from each other, the divergence within each pixel-beam 115, the expected angle of diffraction caused by object 140, the distance from source 110 to a detector 170, and the spatial sensitivity of detector 170. The distance between centers of apertures 123 should be such that the diffraction patterns around two adjacent pixel-beams 115 do not overlap at detector 170. However, some overlap is acceptable because mathematical analysis of the intensity patterns can separate radiation diffracted from different pixel-beams 115.

For some types of imaging of object 140, the amount of diffracted radiation is represented in the image, and diffracted radiation from a pixel-beam can overlap with diffracted radiation from a neighboring pixel-beam to increase optical density in the image. Allowing an overlap increases: the number of pixel-beams 115 passing through object 140; the fraction of radiation from source 110 used for imaging in apparatus 100; and the portion of object 140 probed by a single exposure.

Pixel-beams 115 pass through and interact with the matter of object 140. In the course of the interaction radiation of each pixel-beam 115 is partly absorbed, partly refracted, partly non-coherently scattered, and partly diffracted by ordered structures of object 140. Absorption modulates the intensity of a resulting image as in conventional imaging technology. A spatial filter 150 blocks the refracted portion of the pixel-beam and portion which did not interact with matter in object 140.

Spatial filter 150 is between object 140 and detector 170 and contains opaque regions 158 which are attached to intersections in a mesh (not shown). Alternatively, opaque regions 158 could be attached to a transparent material which does not scatter, diffract, or absorb the radiation from source 110. Opaque regions 158 are positioned where pixel-beams 115 would cross the plane of spatial filter 150 if object 140 was absent, and the sizes of regions 158 are selected to block radiation in non-deflected radiation and radiation refracted in object 140. Regions 158 have a shape (circular, square, or other) corresponding to the shape of apertures 123 and 133 in spatial filters 120 and 130.

One embodiment of spatial filter 150 contains regions 158 that are circular caps having the form of cake pans, built from highly absorbing material. The bottom of each caps has radius R, which is $$R = B + r + d,$$

where B is radius of pixel-beam 115 at the plane of spatial filter 150, r is the broadening of pixel-beam 115 caused by refraction in object 140, and d is the additional broadening which may be caused by diffraction at the edges of apertures 133. In one implementation, value r is the displacement caused by about a 10 arc second angle and cuts off all refracted radiation. The walls of the caps are formed from the same material as the bottom and have a height several times the radius R of the bottom, 4*R in some embodiments. The walls of the caps prevent radiation scattered from the cap's bottom from irradiating object 140 or detector 170.

Spatial filter 150 also includes optional opaque regions 159 which surround opaque regions 158 and block radiation diffracted at large angles. Radiation reaching detector 170 passes through annular openings 153 in spatial filter 150 between opaque regions 158 and 159. A spatial filter 160 placed after spatial filter 150 and before detector 170 also has opaque regions 168 and 169 which are separated by annular openings 163. Opaque regions 168 correspond to opaque regions 158, and opaque regions 169 correspond to opaque regions 159. The combination of opaque regions 158, 159, 168, and 169 filter out diffracted radiation which is diffracted at angles outside a range of particular interest for structural analysis. By selecting the sizes of opaque regions 158, 159, 168, and 169, a specific range of angles of diffracted radiation can be detected. The resulting diffraction pattern which is available for measurement at detector 170 could, for example, be a set of diffraction reflexes which identify particular types of structures or chemicals with object 140.

The angles of radiation detected by detector 170 can be varied by changing spatial filters 150 and 160. In one embodiment of the invention, regions 158 have adjustable size and can be expanded to filter radiation which is diffracted at angles less than some particular angle of the specific interest for structural investigation. In another embodiment of the invention, spatial filters 150 and 160 are movably mounted so that the distances between spatial filter 150 and spatial filter 160, and from object 150 to spatial filter 150 or 160 can be varied.

For imaging, the brightness of a pixel in an image is proportional to the intensity of radiation diffracted from a corresponding pixel-beam. Spatial filter 160 and regions 159 can be removed to allow all diffracted radiation to pass to detector 170 so that all of the diffracted radiation is harvested and a brighter image results. Since the intensity of diffracted radiation decreases with increasing angle, large angle diffracted components can be effectively removed from an image formed on film, by controlling exposure time so that the large angle components do not significantly expose the film.

Detector 170 is a conventional detector such as a photofilm, a luminescent screen and optical system for measuring or recording light resulting when penetrating radiation strikes the luminescent screen, or a pixellated two-dimensional detector adapted for the type of radiation from source 110. For structural analysis of object 140, digital detectors facilitate numerical processing of measurements of the diffraction pattern. Typically, a general purpose computer (not shown) such as a personal computer or special purpose analyzer may be connected to detector 170 to perform the required analysis.

Russian patent application No. 94042608/25 (042777), entitled "Method of Obtaining an Object Projection by Means of Penetrating Radiation and an Apparatus for its Implementation", filed Nov. 30, 1994, by Alexey V. Kurbatov and Pavel I. Lazarev, describes detector systems for dark field imaging and analysis of penetrating radiation and is incorporated by reference herein in its entirety. The detectors described in Russian application No. 94042608/25 (042777) can be employed of the present invention.

In an exemplary embodiment of apparatus 100, source 110 is an X-ray source which emits radiation having wavelength of 0.3 Å from a focal area having a radius of 10 microns. Spatial filter 120 is 0.2 m from source 110 and has circular apertures 123 with radius of 10 microns and center-to-center distance of 45 microns. Spatial filter 120 is made of a material such as lead (Pb) or zirconium (Zr) which is good absorber of 0.3 Å X-rays. The material of a spatial filter is desired to be a good absorber of the radiation with relatively little scattering at the wavelength of the radiation used. The X-rays absorption and scattering properties of many materials are listed in commonly used handbooks dealing X-ray physics and structural analysis. See, for example, "The Powder Methods in X-ray Crystallography" by L. V. Azaroff and M. J. Buerger, 1958, London, Toronto. The thickness of spatial filter 120 depends on the material used, and for the case of lead is about 750 microns.

In the exemplary embodiment, spatial filter 130 is absent, and spatial filter 150 is 0.09 m from spatial filter 120. Object 140 has a thickness of about 0.06 m and a front edge that is next to spatial filter 120, making the back edge of object 140 0.03 m from spatial filter 150. With this geometry, undeflected pixel-beams have a radius of 19 microns and a center-to-center distance of about 65 microns at the plane of detector 170. Opaque regions 158 in spatial filter 150 have radius of 21 microns which is slightly larger the radius of the initial beam at the plane of spatial filter 120. Regions 159 are absent, and gaps between regions 158 which are about 23 microns wide allow diffracted radiation to pass through spatial filter 150 to detector 170. In the exemplary embodiment, opaque regions 158 are caps having walls extending toward object 140. The walls stop radiation at large angles, which could otherwise pass through spatial filter 150. The walls on a region 158 reduce the angle of radiation which can pass through an adjacent gap in spatial filter 150. Accordingly, adding walls to opaque regions 158 makes spatial filter 150 more angle sensitive. Spatial filter 160 can be added to further increases angle sensitivity. By choosing distances and sizes of components in filters 150 and 160, one can create filter systems of different angle sensitivity.

Table 1 indicates diffraction angles and reflex radii, at spatial filter 150 in the exemplary embodiment, for reflexes of typical biological materials. Material at the front edge of object 140 (left edge in FIG. 1) produces larger reflexes than material at the back edge of object 140 because the back edge is closer to spatial filter 150.

TABLE 1.

| Periodicity D (material) | Diffraction Angle 2θ | Radius of reflex from front edge diffraction | Radius of reflex from back edge diffraction |
| --- | --- | --- | --- |
| 48 Å (mucus) | 0.36° | 560 μm | 180 μm |
| 143 Å (muscle) | 0.12° | 180 μm | 60 μm |
| 200 Å (cartilage) | 0.08° | 126 μm | 40 μm |
| 429 Å (muscle) | 0.04° | 63 μm | 20 μm |

In some embodiments, spatial filters 150 and 160 remove reflexes having large radii that spread radiation across multiple pixels. This improves image resolution because radiation from each pixel beams is confined to a smaller area in the image. For example, spatial filters 150 and 160 can remove the radiation that forms the reflex from mucus corresponding to periodicity of 48 Å. This reflex has a large angle of diffraction (0.36°) which creates at spatial filter 150 a large reflex (560 microns) when diffraction takes place at the front edge of object 140. About ten different gaps between regions 158 receive radiation from this reflex of mucus which blurs the image across ten pixels. Accordingly, the resolution of a projection is lower using the reflex corresponding to 48 Å periodicity in mucus than the resolution using a reflex corresponding to a longer periodicity. For example, a reflex for mucus corresponding to periodicity 90 Å, which is not listed in the table above, is about as bright as the reflex for periodicity of 48 Å and has a reflex radius of about 390 microns. This provides almost twice the resolution as the 48 Å reflex.

Placing object 140 closer to spatial filter 150 also enhances resolution. Resolution (or the size of the reflex from diffraction at the front edge of object 140) improves by a factor 1.3 if the back edge of object is 0.01 m from filter 150 instead of 0.03 m. Reflexes from the back edge of object 140 are 3 times smaller. Smaller wavelengths create better resolution because all reflexes are diffracted at smaller angles and resolve details with better accuracy. Tomography or analysis of multiple projections of object 140 from different angles can also improve resolution of the diffracting tissue.

The embodiment of FIG. 1 contains spatial filters 120, 130, 150, and 160 and detector 170, all of which are planar. Alternatively, spatial filters 120, 130, 150, and 160 and detector 170 can be spherical in form which corresponds to the form of the radiation front emitted by source 110. In this case, spatial filters 120, 130, and 160 are portion of spheres of absorptive material, centered on source 110, and containing regularly spaced apertures. For spherical spatial filters, apertures having the same size transmit equal amounts of radiation. For planar filters, the angle of incidence and intensity of radiation changes with distance from source 110. To provide uniform intensity pixel-beams 115 in some embodiments, the size and shape of apertures 123, 133, 153, and 163 vary across the surface of the spatial filters 120, 130, 150, and 160.

In a second exemplary embodiment, source 110 is at the center of semi-spherical spatial filter 120, and the distance between source 110 and spatial filter 120 is such that apertures 123 create pixel-beams 115 that diverge from each other and have a center-to-center separation at spatial filter 150 that is larger than the radius of the reflexes produced by object 140. With this geometry, the diffraction patterns can be used for imaging of object 140 and/or for detailed analysis of the angular and axial distributions of intensity in a diffraction pattern from each pixel-beam 115.

In addition to structural analysis and forming images of object 140 using a single projection of pixel-beams 115 through object 140, object 140 can be rotated to form multiple projections. Well known tomography techniques can be employed to provide three-dimensional maps of the structure of object 140.

Figure 3:
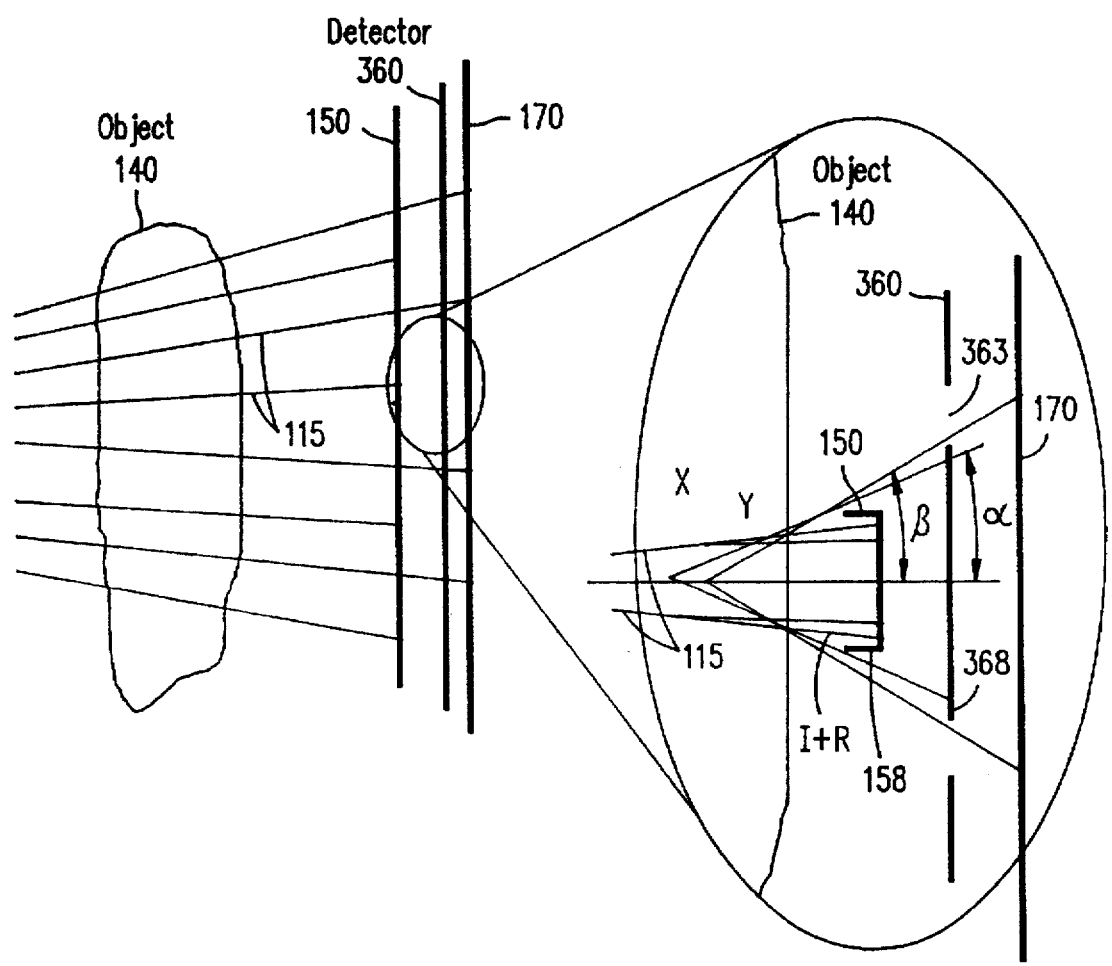
FIG. 3 shows scattering of radiation in an object and an embodiment of spatial filters which discriminate an angular range of diffracted radiation for imaging or analysis.
Figure 4:
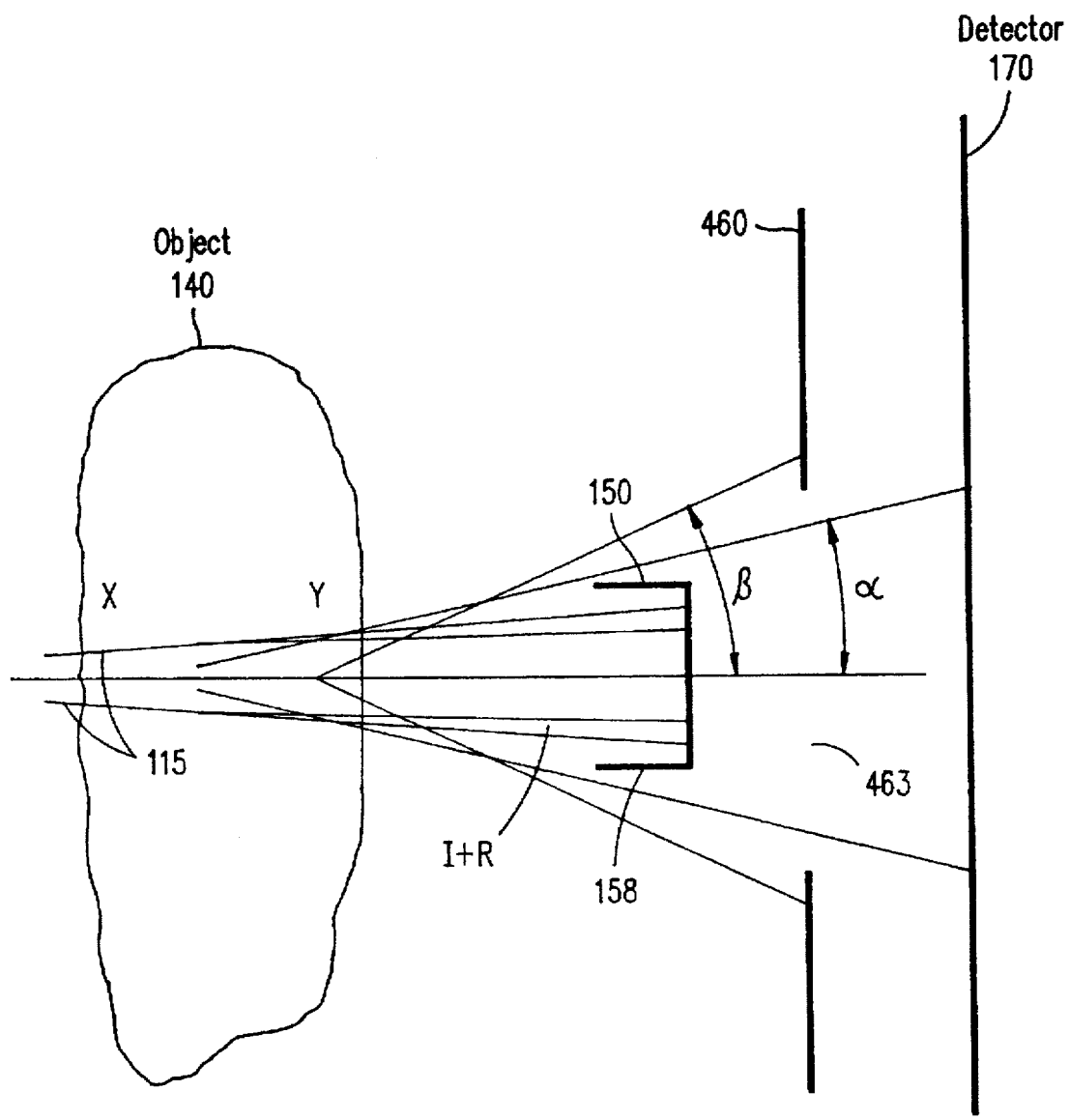
FIG. 4 shows another embodiment of the spatial filters which select radiation for imaging or analysis.

FIGS. 3 and 4 show alternative embodiments of spatial filters between object 140 and detector 170. A pixel-beam has a portion I+R which either did not interact with object 140 or was refracted by object 140. Portion I+R is blocked by region 158. The non-coherently scattered portion of radiation is typically deflected at angles larger than the diffraction angles, and is absorbed by a spatial filter 360 (FIG. 3) or a spatial filter 460 (FIG. 4).

The embodiment of FIG. 3 differs from the embodiment of FIG. 4 in that spatial filter 360 contains opaque regions 368 in central portions of each aperture 363 and in that apertures 363 in spatial filter 360 are larger than apertures 463 in spatial filter 460. By changing form and size of opaque regions 368 and/or apertures 363, a desired angular range of diffracted light can be selected for detection by detector 170 to obtain images or analysis of particular diffraction angles.

FIGS. 3 and 4 show diffracted radiation for two types of structures inside object 140, one structure X diffracts radiation at an angle α and another structure Y diffracts radiation at an angle β. Spatial filter 360 blocks radiation at angle α for imaging object 140 using radiation diffracted at angle β.

Spatial filter 460 blocks radiation at angle β for imaging of object 140 using radiation diffracted at angle α. Imaging object 140 twice, once with spatial filter 360 and once with spatial filter 460, shows the presence and locations of structures X and Y. The two step process eliminates overlapping of radiation which could obscure the location of structure X or Y.

A non-invasive imaging process using apparatus 100 for detecting the presence of an abnormal tissue such as cancer in a patient can be implemented using measurable differences in the diffraction patterns for normal and abnormal tissue. For example, normal and sickle anemic erythrocytes have distinct diffusive scattering patterns. Similarly, mucus from normal and from sub-lethal irradiated rats have different distinct diffraction patterns. To identify and locate abnormal tissue, a patient can be imaged using a spatial filter 360 that selects radiation diffracted at an angle β known to be present in the diffraction pattern for the abnormal tissue. Spatial filter 360 is replaced with spatial filter 460 to select radiation diffracted at angle α present in the diffraction pattern of normal tissue, and the patient is imaged again. The two images can be compared to determine the presence and location of abnormal tissue relative to normal tissue.

Although the present invention has been described with reference to particular embodiments, the description is only an example of the invention's application and should not be taken as a limitation. In particular, even though much of preceding discussion was aimed at forming images using X-ray radiation, alternative embodiments of the invention include use of other penetrating radiations such as neutrons which have wavelengths similar to X-rays. Various other adaptations and combinations of features of the embodiments disclosed are within the scope of the present invention as defined by the following claims.

We claim:

1. A method for examining the structure of an object, comprising:

irradiating the object with a plurality of beams, wherein the beams are separated from each other and simultaneously pass through the object;

detecting, for each of the beams, an intensity of diffracted radiation around a non-deflected path of the beam; and forming an image of the object, Wherein the image comprises an array of pixels such that each pixel is associated with one of the beams and has an intensity that indicates the intensity of diffracted radiation around the non-deflected path of the associated beam.

2. The method of claim 1, wherein detecting intensity for a beam comprises measuring an integral of the intensity of the diffracted radiation around the non-deflected path of the beam.

3. The method of claim 1, further comprising filtering radiation which exits from the object to remove radiation not deflected by the object, wherein filtering occurs before detecting intensity.

4. The method of claim 1, wherein irradiating the object comprises irradiating the object with beams that are sufficiently separated that diffraction patterns caused by diffraction of neighboring beams in the object do not overlap where diffracted intensity is detected.

5. The method of claim 1, wherein detecting intensity for a beam comprises:

blocking radiation which is outside a range of angles with the beam; and measuring intensity of radiation within the range of angles.

6. The method of claim 1, further comprising irradiating a first spatial filter with a penetrating radiation, wherein the first spatial filter has a first array of apertures formed therethrough and radiation which passes through the first array of apertures forms the beams.

7. A method for examining the structure of an object, comprising:

irradiating a first spatial filter with a penetrating radiation from a radiation source, wherein the first spatial filter has a first array of apertures formed therethrough and radiation which passes through the first array of apertures forms a plurality of beams that are separated from each other and diverge from each other;

irradiating a second spatial filter with the penetrating radiation that passes through the first array of apertures, wherein the second spatial filter has a second array of apertures formed therethrough, wherein each aperture in the second array is centered along a line that passes through the source and a center of a corresponding aperture in the first array;

irradiating the object with the plurality of beams, wherein the beams simultaneously pass through the object; and detecting, for each of the beams, an intensity of diffracted radiation around a non-deflected path of the beam.

8. A method for examining the structure of an object, comprising:

irradiating the object with a plurality of beams which diverge from each other, wherein the beams are separated from each other and simultaneously pass through the object;

filtering radiation which passes through the object to remove radiation not deflected by the object and radiation refracted in the object, wherein filtering occurs before detecting intensity; and detecting, for each of the beams, an intensity of diffracted radiation around a non-deflected path of the beam.

9. The method of claim 8, wherein detecting intensity for a beam comprises measuring a diffraction pattern around the non-deflected path of the beam.

10. The method of claim 9, wherein measuring the diffraction pattern comprises measuring an angle at which the diffraction pattern has a reflex.

11. A diagnostic procedure comprising:

irradiating a tissue with a first plurality of beams of a penetrating radiation, wherein the beams are separated from each other and simultaneously pass through the tissue;

spatially filtering radiation which exits from the tissue, wherein for each beam, the filtering selects radiation within a first range of angles with non-deflected path of the beam, and the first range includes a first angle that corresponds to a reflex found in a diffraction pattern for an abnormal tissue; and measuring, for each beam, radiation which exits the tissue at the first angle relative to the non-deflected path of that beam.

12. The procedure of claim 11, wherein the beams are divergent from each other.

13. The procedure of claim 11, wherein measuring comprises forming an image of the tissue, wherein the image comprises pixels that correspond to the beams, each pixel having an intensity which depends on an intensity of radiation diffracted from a corresponding beam, at the first angle with the corresponding beam.

14. The method of claim 11, further comprising:

irradiating a tissue with a second plurality of beams of the penetrating radiation, wherein the second plurality of beams simultaneously pass through the tissue;

measuring, for each beam in the second plurality, radiation which exits the tissue at a second angle relative to a non-deflected path of that beam, wherein the second angle corresponds to a reflex found in a diffraction pattern for a normal tissue; and comparing the measurement of the radiation at the first angle to the measurement of the radiation at the second angle.

15. An apparatus for examining an object, comprising:

a source of penetrating radiation;

a first spatial filter positioned to divide radiation from the source into a plurality of separate beams which simultaneously irradiate the object;

a second spatial filter positioned to filter radiation from the beams which emerges from the object, the second spatial filter having an array of separate regions which are opaque to the penetrating radiation, wherein each opaque region corresponds to one of the beams and is positioned and sized to block radiation from the corresponding beam which passes undeflected through the object and block radiation from the corresponding beam which is refracted by the object; and a detector of the penetrating radiation positioned to measured radiation from the beams, which passes through the second filter.

16. The apparatus of claim 15, wherein the first spatial filter comprises a layer of material which is opaque to the penetrating radiation, the layer having an array of apertures formed therethrough.

17. The apparatus of claim 16, further comprising a third spatial filter which comprises an opaque layer having an array of apertures formed therethrough, wherein each aperture through the third spatial filter is along a line through the source and a corresponding one of the apertures in the first spatial filter and is larger than the corresponding aperture in the first spatial filter.

18. The apparatus of claim 16, wherein the layer of material is formed in the shape of a portion of a sphere centered on the source.

19. The apparatus of claim 15, wherein each opaque region of second spatial filter comprises:

a bottom region having a normal parallel to an undeflected direction of the corresponding beam; and a wall which surrounds a perimeter of the bottom region.

20. The apparatus of claim 15, wherein the opaque regions have a size which can be adjusted by a user.

21. The apparatus of claim 15, wherein the second spatial filter further comprises a layer of material which is opaque to the penetrating radiation, wherein the layer has an array of apertures formed therethrough, and each of the opaque regions is located in a central portion of one of the apertures through the layer and is surrounded by an area which is transparent to the penetrating radiation.

22. The apparatus of claim 21, wherein the layer of material is formed in the shape of a portion of a sphere centered on the source.

* * * * *